United States Patent [19]

Elazhary et al.

[11] Patent Number: 6,060,457
[45] Date of Patent: May 9, 2000

[54] DNA PLASMID VACCINE FOR IMMUNIZATION OF ANIMALS AGAINST BVDV

[75] Inventors: Youssef Elazhary; Serge Harpin, both of Saint-Hyacinthe; Brian Talbot, Lennoxville; Majambu Mbikay, St-Bruno, all of Canada

[73] Assignee: Universite de Montreal, Montreal, Canada

[21] Appl. No.: 08/967,315

[22] Filed: Oct. 28, 1997

Related U.S. Application Data

[63] Continuation of application No. 08/667,869, Jun. 20, 1996, abandoned.

[51] Int. Cl.[7] .............................. A61K 48/00; C12N 7/00; C12N 15/85
[52] U.S. Cl. ....................... 514/44; 435/320.1; 435/235.1
[58] Field of Search .............................. 536/23.1; 514/44; 424/93.1; 435/235.1, 320.1

[56] References Cited

U.S. PATENT DOCUMENTS

| | | | |
|---|---|---|---|
| 5,494,807 | 2/1996 | Paoletti et al. | 435/69.3 |
| 5,733,745 | 3/1998 | Kowalski et al. | 435/69.3 |

FOREIGN PATENT DOCUMENTS

| | | | |
|---|---|---|---|
| WO 95/12682 | 5/1995 | WIPO | 424/204.1 |

OTHER PUBLICATIONS

Collett et al., 1988, *Virology*, 165:191–199.
Donnelly et al., 1994, *J. Immunol. Methods*, 176:145–152.
Harpin et al., 1995, *Arch. Virol.*, 140:1285–1290.

Kozak, 1991, *J. Biol. Chem.*, 266(30):19867–19870.

Cohen, Jon. Naked DNA points way to vaccines, Science vol. 259, pp. 1691–1692, Mar. 19, 1993.

McDonnell et al. Molecular Medicine DNA vaccines. New England Journal of Medicine vol. 334 No. 1 pp. 42–45, Jan. 4, 1996.

Thompson, Larry. A shot in the arm for vaccine problems. The Washington Post section A p. 3, Jun. 7, 1993.

NIH Panel, Report and Recommendations of the Panel to assess the NIH investment in Research on gene therapy, Dec. 7, 1995.

Wiskerchen, et al. Pestivirus Gene Expression: the First Protein Product of the Bovine Viral Diarrhea Virus large open reading frame, p20, possesses proteolytic activity. J. of Virol. vol. 65, No. 8, pp. 4508–4514, Aug. 1991.

*Primary Examiner*—Deborah J. Clark
*Attorney, Agent, or Firm*—Swabey Ogilvy Renault

[57] ABSTRACT

The present invention relates to a DNA plasmid vaccine for immunization of animals against BVDV which comprises at least a mammalian expression vector having a DNA sequence encoding at least one BVDV immunogenic protein or fragment thereof which is selected from the group consisting of BVDV major glycoprotein gp53/E2, p20 (Npro), p14/C, gp48/E0, gp25/E1 and p80/NS3 proteins, the immunogenic protein is operably linked downstream from a suitable promoter for its expression, whereby inducing a BVDV-specific antibody responses.

3 Claims, No Drawings

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:1:

GGGATCCACC ATGGTACAGG GCATTCTG                           28

-continued (2) INFORMATION FOR SEQ ID NO:2:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:2:

GTCTAGACTA TAAGAGTAAG ACCCACTT                    28

DNA PLASMID VACCINE FOR IMMUNIZATION OF ANIMALS AGAINST BVDV

This application is a continuation of application Ser. No. 08/667,869 filed Jun. 20, 1996, abandoned.

BACKGROUND OF THE INVENTION (a) Field of the Invention

The invention relates to DNA-based immunization technology for the vaccination of animals against BVDV.

(b) Description of Prior Art

Bovine viral diarrhea virus (BVDV), an economically important pathogen of cattle, is an enveloped single-stranded RNA virus classified as a member of the genus Pestivirus within the Flaviviridae family. The BVDV genome is approximately 12.5 kb in length and contains one large open reading frame (ORF). The ORF codes for a large polyprotein of approximately 450 kDa which is processed co- and post-translationally by either host and viral proteases. The N-terminal end of standard BVDV polyprotein results in a non-structural protein p20 (Npro), capsid protein p14 (C); envelope glycoproteins gp48 (E0), gp25 (E1), gp53 (E2); non-structural proteins p125 (NS23), p10 (NS4A), p32 (NS4B), p58 (NS5A) and p75 (NS5B). BVDV may exist in two biotypes, cytopathic or non-cytopathic. The two biotypes differ by the production of an 80 kDa polypeptide (non-structural protein p80, NS3) by the cytopathic BVDV. Recently, based on the antigenic and genomic studies, subgroups of BVDV appear to represent two different genotype (1 and 2).

BVDV, like other RNA viruses such as influenza, are known for their high antigenic variation. These BVDV variants that evolve through immune selective pressure may lead to the incomplete protection often observed after conventional vaccination. This antigenic diversity raises the challenge to always includes in the next vaccine, the new antigenic BVDV variant. This antigenic variability of BVDV strains has created the demand for a new generation of vaccines.

A number of monoclonal antibodies directed against the BVDV major glycoprotein gp53 (E2) have been shown to possess virus-neutralizing activity.

Direct injection of DNA into animals is a novel and promising technology for delivering specific antigens for immunization. This approach has recently been shown to induce both humoral and cellular immune responses against several infectious agents, such as influenza, rabies, human immunodeficiency, bovine herpes viruses, and malaria.

However, it would be highly desirable to be provided with a plasmidic expression vector having the immunogenic potential of the BVDV genotype 1 gp53 (E2) protein or another BVDV immunogenic protein when injected into mice without presenting the drawbacks of the conventional vaccination.

SUMMARY OF THE INVENTION

One aim of the present invention was to determine whether direct injection of naked DNA (in the exemplified case encoding the BVDV genotype 1 gp53 (E2) protein) into muscle and skin could induce an immune response to BVDV.

In accordance with the present invention, it is demonstrated that the immunologic treatment with naked DNA (encoding at least one protein or an immunogenic fragment thereof selected from the group consisting of BVDV genotype 1 gp53 (E2), p20 (Npro), p14/C, gp48/E0, gp25/E1 and p80/NS3 proteins) induced a BVDV specific antibody response to both biotypes (cytopathic and non-cytopathic) of BVDV genotype 1, and to cytopathic BVDV genotype 2.

The preferred BVDV immunogenic protein used in accordance with the present invention is BVDV genotype 1 gp53 (E2) or an immunogenic fragment thereof.

Also in accordance with the present invention BVDV-neutralizing antibodies were also generated but only against BVDV genotype 1 strains.

In accordance with the present invention there is provided a DNA plasmid vaccine for immunization of animals against BVDV which comprises at least a mammalian expression vector having a DNA sequence encoding at least one BVDV immunogenic protein or fragment thereof which is selected from the group consisting of BVDV major glycoprotein gp53/E2, p20 (Npro), p14/C, gp48/E0, gp25/E1 and p80/NS3 proteins, the immunogenic protein is operably linked downstream from a suitable promoter for its expression, whereby inducing a BVDV-specific antibody responses.

In accordance with the present invention there is provided a method of immunizing an animal against BVDV which comprises the steps of:

a) preparing a mammalian expression vector having a DNA sequence encoding at least one BVDV immunogenic protein or a fragment thereof selected from the group consisting of BVDV major glycoprotein gp53/E2, p20 (Npro), p14/C, gp48/E0, gp25/E1 and p80/NS3 proteins, the protein or fragment thereof is operably linked downstream from a suitable promoter for its expression; and b) administering intramuscularly or intradermally to the animal the expression vector;

whereby inducing BVDV-specific antibody responses into the animal.

The term "BVDV immunogenic protein" refers to an immunogenic protein which would result in a specific BVDV-specific antibody responses into the animal pursuant to the administration of the vector. Such an immunogenic protein or a fragment thereof may be selected from the group consisting of BVDV major glycoprotein gp53/E2, p20 (Npro), p14/C, gp48/E0, gp25/E1 and pB0/NS3 proteins.

The vaccine of the present invention may further comprise a pharmaceutically acceptable carrier for its intramuscular (IM) or intradermal (ID) administration to the animal. Such a carrier may be selected, without limitation, from the group consisting of phosphate buffer saline (PBS), golden particles and water.

Any mammalian expression vector may be used in accordance with the present invention. More specifically, the vector may be selected, without limitation, from the group consisting of pcDNA3 and pcDNA/gp53/E2.

Any promoters suitable for cloning and expression of the BVDV immunogenic protein may be used in accordance with the present invention. More specifically, the promoter may be selected, without limitation, from the group consisting of human cytomegalovirus (CMV) intermediate early promoter and PC2 (proprotein convertase 2).

The most preferred promoter is human cytomegalovirus (CMV) intermediate early promoter.

DETAILED DESCRIPTION OF THE INVENTION

Bovine viral diarrhea virus (BVDV) is an economically important and worldwide distributed pathogen in cattle which has not been controlled by classical vaccination. The region encoding the BVDV major glycoprotein gp53 (E2) known to possess virus-neutralizing activity, was cloned into a mammalian expression vector under the human cytomegalovirus (CMV) intermediate early promoter. Intramuscular (IM) and intradermal (ID) administration routes to the recombinant plasmid DNA into BALB/c mice induced a BVDV gp53-specific antibody responses to both biotypes (cytopathic and non-cytopathic) of BVDV genotype 1, and to cytopathic BVDV genotype 2. BVDV-neutralizing antibodies were also generated but only against BVDV genotype 1 strains.

Viruses

The BVDV strains used are from two subgroups, genotype 1 and 2. Each genotype is represented by two biotypes, cytopathic (c) and non-cytopathic (nc). Genotype 1 strains NADL (c, ATCC accession number VR-534) and New-York (nc, ATCC accession number VR-524) were obtained from the American Type Culture Collection (ATCC, 12301 Parklawn Drive, Rockville, Md., 20852 U.S.A.); genotype 2 strains BVDV2/145 (c) and BVDV2/890 (nc), were kindly provided by Dr. Frey (Central Veterinary Laboratory, USDA, Ames, Iowa, USA).

Cells

Bovine turbinate (BT) cell line free of BVDV was cultured in Earle's minimum essential medium (MEM, GIBCO Canada Inc.). This medium was supplemented with 1 mM sodium pyruvate, 0.5% lactalbumine, 1.5 g/L sodium bicarbonate, 2.4 mM glutamine, and 8% Fetal Bovine Serum (FBS; Hyclone Laboratories Inc.). COS-7 cell line was cultured in Dulbecco modified Eagle medium (DMEM, GIBCO Canada Inc.), and 10% FBS.

Cloning of the BVDV genotype 1 gp53 gene

RNA extraction and cDNA synthesis of BVDV/NADL strain were performed as described by Harpin et al. (1995, Arch. Virol., 140:1285–1290). NADL cDNA product was used as a template for amplification of the gp53 region (nucleotides 2414–3725) according to NADL sequence (Collett et al., 1988, Virology, 165:191–199). The sense primer (GGGATCCACCATGGTACAGGGCATTCTG; SEQ ID NO:1) contains the BamHI restriction enzyme site and a Kozak translation initiation sequence (Kozak, 1991, J. Biol. Chem., 266(30):19867–19870). The antisense primer (GTCTAGACTATAAGAGTAAGACCCACTT; SEQ ID NO:2) contains the XbaI restriction enzyme site and a stop codon. After digestion with these two enzymes, the gp53 PCR product, was inserted into the BamHI and the XbaI sites of the pcDNA3 mammalian expression vector (InVitrogen, San Diego, Calif.).

Cell Transfection and Protein Expression

COS-7 cells were transfected with pcDNA/gp53 DNA by lipofection (LipofectAMINE, Gibco BRL) according to the manufacturer's instructions. Briefly, plasmid DNA (2 mg) and liposomes (10 ml; 2 mg/ml) were diluted separately into 100 ml of DMEM without antibiotics and FBS. These aliquots were mixed and incubated at room temperature (RT) for 30 minutes. The DNA/liposome complexes were diluted with 800 ml of transfection medium and the mixture was slowly added to the cells in 35-mm wells of 6-well tissue cultures dishes. The cells were rinsed with the same transfection medium prior to addition of complexes. They were incubated at 37° C. under 2% $CO_2$. After a 5 h incubation, 1 ml of transfection, medium supplemented with 20% of FBS was added and the incubation was resumed for another 18 h. Then, the medium was changed with fresh DMEM supplemented with 10% of FBS (without antibiotic). Twenty-four, forty-eight, and seventy-two hours after transfection, the cells were washed with PBS and acetone fixed. Expression of the glycoprotein gp53 was monitored by indirect immunofluorescent (IF) staining technique for BVDV antigen. Briefly, polyclonal bovine anti-BVDV serum (1:50) was added for 30 minutes at 37° C. and cells were washed twice with PBS and once with distilled water.

This was followed by a 30 minute incubation at 37° C. with a fluorescein-conjugated rabbit anti-bovine immunoglobulin G (1:50). Cells were washed twice with PBS and once with distilled water. COS-7 cells transfected with plasmid pcDNA3 were used as a negative control.

Immunization of Mice

Female 6-week-old BALB/c mice were purchased from Jackson Laboratory, Bar Harbor, Maine. Each mouse was injected either intramuscularly (thigh muscle) or intradermally (dorsal epidermis tissue) with 100 ug of either plasmid DNA pcDNA/gp53, pcDNA3 (plasmid control) or with $10^5$ $TCID_{50}$ of BVDV/NADL strain. The injection was repeated 2 weeks later. Blood samples from each mouse were collected by retroorbital puncture.

Antibody Response in Immunized Mice

Sera from immunized mice were pooled and tested for antibody against both BVDV genotypes and biotypes by peroxidase-linked antibody assay (PLA assay). BT cells grown in 96-well tissue culture plates were infected with each of the BVDV strains ($10^2$ $TCID_{50}$/well). After a 3 day incubation, the cells monolayers were washed with PBS-Tween™ (0.05% Tween™ 20, Sigma, Mississauga, Ontario), fixed by the addition of 100 ml/well of acetone (20%) for 10 min., and dried at 30° C. for 3 hours. They were washed again with PBS-Tween™ and dried at room temperature (RT). Each well was incubated with 100 ml of pooled mice sera (1:10) for 10 min. at 30° C. Plates were then washed threes times with PBS-Tween™ and dried at RT. For the detection of bound gp53-specific antibodies, 100 ml/well of goat anti-mouse IgG (H+L) Horseradish peroxydase conjugate (BIO-RAD, Mississauga, Ontario) diluted 1:20 was added and incubated for 10 min. at RT. Plates were washed three times with PBS-Tween and dried at RT. Finally, the substrate (3-amino-9-ethylcarbazole, Sigma, Mississauga, Ontario) and hydrogen peroxide in 0.05 M acetate buffer (pH 5) were added. After a 10 min. incubation, the plates were subjected to microscopic examination. Each serum was tested in duplicate.

Neutralization Assay for BVDV-Specific Antibodies

Sera were inactivated for 30 min. at 56° C. One hundred $TCID_{50}$ of each BVDV strain was preincubated with serial dilutions (1:10 to 1:80) of mouse antisera for 1 h at 37° C. Following incubation, the antiserum-virus mixture (50 ml) was added to each well. The cell culture was incubated for 1 h at 37° C. Then, MEM medium was added to the cells and incubated at 37° C. with 2% $CO_2$ for 3 days. Each serum dilution was tested in duplicate. The highest dilution that completely inhibited the virus cytopathic effect in at least 50% of the culture was considered as the virus neutralization titer. For testing the non-cytopathic BVDV strains, after 3 days the plates were stained by PLA assay as described above.

Expression of the BVDV gp53 (E2) Gene in COS Cells

Expression of the BVDV gp53 (E2) gene was analyzed in COS cells transiently transfected with the plasmid DNA construct pcDNAgp53 containing the CMV promoter and the bovine growth hormone-polyadenylation sequences. The cytoplasmic expression of the BVDV major glycoprotein gp53 (E2) in transfected cells was intense and can be detected by IF staining after only 24 h. About 50% to 80% of the cells showed signs of the BVDV gp53 protein. Forty-eight hours after transfection, COS-7 cells were assayed by IF.

BVDV-Specific Antibody Responses by DNA Injection of pcDNA/gp53

Intramuscular (IM) and intradermal (ID) routes of DNA administration were tested for their ability to raise an immune response against the BVDV major glycoprotein gp53 (E2) in mice. Groups of mice were injected in the thigh muscle or the dorsal epidermis tissue with 100 ug of vector DNA (pcDNA/gp53); they were boosted 14 days later with an additional 100 ug of vector. Mice were bled 2 weeks after the first injection, and 4 to 6 weeks after the second injection. Antibody responses were assayed using the PLA test. In addition, sera were tested for BVDV-neutralization antibodies.

In both experimental approaches, sera from mice-injected with plasmid DNA (pcDNA3) were used as negative controls and sera from mice immunized with BVDV/NADL virus were used as positive controls. Table 1 shows that BVDV-specific antibodies were generated by either IM/ID injections and were able to detect BVDV genotype 1 strains NADL (c) and New-York (nc), and genotype 2 strains BVDV2/145 (c), but not BVDV2/890 (nc).

TABLE 1

BVDV-specific antibody generated by injection of pcDNA/gp53

| Material injected and route of injection | Time of bleed | Signs of BVDV-specific antibody against different BVDV strains | | | |
|---|---|---|---|---|---|
| | | genotype 1 | | genotype 2 | |
| | | NADL | New-York | BVDV2/145 | BVDV2/890 |
| Virus/NADL | | | | | |
| i.m. | 2 | − | − | − | − |
| | 4 | nd | nd | nd | nd |
| | 6 | + | + | + | − |
| | 8 | + | + | + | − |
| i.d. | 2 | − | − | − | − |
| | 4 | nd | nd | nd | nd |
| | 6 | + | + | + | + |
| | 8 | + | + | + | + |
| pcDNA/gp53 | | | | | |
| i.m. | 2 | − | − | − | − |
| | 4 | nd | nd | nd | nd |
| | 6 | + | + | + | − |
| | 8 | + | + | + | − |
| i.d. | 2 | − | − | − | − |
| | 4 | nd | nd | nd | nd |
| | 6 | + | + | − | − |
| | 8 | + | + | − | − |
| pcDNA3/control | | | | | |
| i.m. | 2 | − | − | − | − |
| | 4 | nd | nd | nd | nd |
| | 6 | − | − | − | − |
| | 8 | − | − | − | − |
| i.d. | 2 | − | − | − | − |
| | 4 | nd | nd | nd | nd |
| | 6 | − | − | − | − |
| | 8 | − | − | − | − |

Signs of BVDV-specific antibody are scored as follows:
+, positive detection;
−, no detection;
nd, not done.
*i.m., intramuscular;
i.d., intradermal.

Microscope visualization of PLA assay showed that sera induced by pcDNA/gp53 ID injection gave a lower level of antibodies compared to IM injection. Six weeks after the first injection, sera were assayed by PLA for the detection of BVDV-specific antibody.

Data in Table 2 shows that at week 6, sera (diluted 1:20) from mice immunized with pcDNA/gp53 by IM injection generated BVDV-neutralizing antibodies only against the BVDV genotype 1 strains (NADL and New-York).

TABLE 2

Induction of BVDV-neutralizing antibodies by pcDNA/gp53

| Material injected and route of injection* | Time of bleed | Signs of BVDV-specific antibody against different BDVD strains | | | |
|---|---|---|---|---|---|
| | | genotype 1 | | genotype 2 | |
| | | NADL | New-York | BVDV2/145 | BVDV2/890 |
| Virus/NADL | | | | | |
| i.m. | 6 | + | + | − | − |
| | 8 | + | + | − | − |
| i.d. | 6 | − | − | − | − |
| | 8 | − | − | − | − |
| pcDNA/gp53 | | | | | |
| i.m. | 6 | + | + | − | − |
| | 8 | + | + | − | − |
| i.d. | 6 | − | − | − | − |
| | 8 | + | + | − | − |
| pcDNA3/control | | | | | |
| i.m. | 6 | − | − | − | − |
| | 8 | − | − | − | − |
| i.d. | 6 | − | − | − | − |
| | 8 | − | − | − | − |

*i.m., intramuscular;
i.d., intradermal

No BVDV-neutralizing antibodies were detectable from mice immunized by ID injection. However at week 8, detectable BVDV-neutralizing antibodies were raised from pcDNA/gp53 ID injection.

Surprisingly, the present invention shows for the first time that an administration of a mammalian expression vector (pcDNA/gp53) encoding the BVDV genotype 1 gp53 (E2) protein under the control of the CMV promoter induces a BVDV-specific antibody response in mice.

DNA immunization with pcDNA/gp53 gave different levels of antibody production depending on the route of injection used. Direct intramuscular inoculation of an aqueous saline solution of plasmid DNA, due to its simplicity and effectiveness, has been widely used and appears to be the most efficient route of immunization (Donnelly et al., 1994, J. Immunol. Methods, 176:145–152). The results of the present invention confirm that intradermal injection induced an immune response in mice although with less efficacy than intramuscular administration. To maximize gene delivery, DNA may be coated onto gold particles and introduced by a method known as particle bombardment or "biolistics". This has been shown to be effective for transferring reporter genes into epidermis, dermis, muscle, liver and pancreas. Another DNA delivery which can be used in accordance with the present invention is the "gene-gun technology" with different BVDV genes to induce protection against BVDV in cattle.

Animals immunized with pcDNA/gp53 generated a cross-neutralization response against both biotypes (cytopathic and non-cytopathic) of BVDV genotype 1 strains. In contrast, BVDV genotype 2 members were not neutralized by the immune mouse sera. Nevertheless, the BVDV-specific antibodies were able to bind to cytopathic BVDV genotype 2 strain as shown by the PLA assay. It has been reported that recombinant baculovirus-expressed gp53 protein from BVDV/Singer strain (genotype 1 member) also failed to induce a neutralization-antibody response against strains of BVDV genotype 2, whereas bacterial recombinant BVDV gp53 protein was unable to generate a strain homologous neutralizing antibodies.

One consequence of immunization using DNA expression vectors is that proteins are necessarily synthesized within the host cell. Therefore, peptides derived from the cytoplasm are processed via the endogenous pathway for presentation by the major histocompatibility complex (MHC) class I molecules leading to the induction of cytotoxic T lymphocytes (CTL). The induction of CTL after administration of DNA expression vectors has been previously demonstrated (Donnelly et al., 1994, J. Immunol. Methods, 176:145–152).

CTL cells recognize epitopes derived from conserved internal viral proteins and they are believed to play a major role in resistance to viral infection. Thus, by recognition of conserved viral epitopes, CTL cells may provide heterologous protection. In order to generate BVDV-specific CTL activity, plasmid DNA expressing the conserved BVDV nucleocapsid protein p14/C could elicit such an immune response.

In accordance with the present invention, the ability to induce an immune response in mice by the injection of an mammalian expression vector carrying the BVDV gp53 gene was demonstrated. The induction of BVDV neutralizing antibody by this new technology, suggest that the structural integrity of the protein is maintained and that it could be possible to obtain a protection in cattle. This shows the feasibility and the potential use of the DNA-based immunization technology into the vaccination field of BVDV.

While the invention has been described in connection with specific embodiments thereof, it will be; understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A method to induce a Bovine Viral Diarrhea Virus (BVDV)-specific antibody response into a mammal which comprises the steps of:

(a) preparing a non-viral mammalian expression vector having a DNA sequence encoding a BVDV gp53/E2 immunogenic protein, wherein said DNA sequence is operably linked downstream from a promoter which induce expression of said BVDV gp53/E2 immunogenic protein; and (b) administering the expression vector intramuscularly or intradermally to the mammal;

whereby said non-viral mammalian expression vector induces a BVDV gp53-specific antibody response into said mammal.

2. The method of claim 1, wherein the promoter is selected from human cytomegalovirus (CMV) intermediate early promoter and PC2 (proprotein convertase 2).

3. The method of claim 1, wherein said DNA sequence is produced by amplification of NADL BVDV strain's cDNA using a sense primer and an anti-sense primer having a sequence of SEQ ID NO:1 and SEQ ID NO:2, respectively.

\* \* \* \* \*